United States Patent [19]

Kakimoto et al.

[11] Patent Number: 5,006,553
[45] Date of Patent: Apr. 9, 1991

[54] AGENT FOR IMPROVING REDUCED FUNCTIONS OF ORGANS CAUSED BY INHIBITED BLOOD CIRCULATION

[75] Inventors: Norihiro Kakimoto, Machida; Kazuo Kumano, Yamato; Kunie Nakamura, Sagamihara, all of Japan

[73] Assignee: Asai Germanium Research Institute Co., Ltd., Tokyo, Japan

[21] Appl. No.: 555,829

[22] Filed: Jul. 23, 1990

Related U.S. Application Data

[63] Continuation of Ser. No. 261,405, Oct. 24, 1988, abandoned.

[30] Foreign Application Priority Data

Oct. 29, 1987 [JP] Japan .................. 62-273747

[51] Int. Cl.$^5$ ............................. A61K 31/28
[52] U.S. Cl. .................................... 514/492
[58] Field of Search ............................. 514/492

[56] References Cited

U.S. PATENT DOCUMENTS 3,689,516  9/1972  Asai et al. .............. 260/429 R
4,279,892  7/1981  Ishida et al. ............ 514/492

FOREIGN PATENT DOCUMENTS 0016444  10/1980  European Pat. Off. .
1257225  3/1969   United Kingdom .
1365997  9/1974   United Kingdom .
2142635  1/1985   United Kingdom .
2143128  2/1985   United Kingdom .
2191697  12/1987  United Kingdom .

*Primary Examiner*—Stanley J. Friedman
*Assistant Examiner*—Raymond J. Henley, III
*Attorney, Agent, or Firm*—Burns, Doane, Swecker & Mathis

[57] ABSTRACT

The present invention provides (1) an agent for improving the reduced functions of organs caused by inhibited blood circulation, characterized by containing, as an effective component, an organogermanium compound represented by the formula (I)

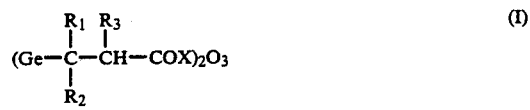

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$ (Y is a metal such as sodium, potassium or the like, or a basic group-containing compound such as lysozyme, basic amino acid or the like), and (2) a method for improving the reduced functions of organs caused by inhibited blood circulation, characterized by administering, in need of such treatment, an effective amount of an organogermanium compound represented by the above formula (I).

6 Claims, 3 Drawing Sheets

AGENT FOR IMPROVING REDUCED FUNCTIONS OF ORGANS CAUSED BY INHIBITED BLOOD CIRCULATION

This application is a continuation, of application Ser. No. 07/261,405, filed Oct. 24, 1988 now abandoned.

BACKGROUND OF THE INVENTION

1. Field of the Invention

The present invention relates to an agent for improving the reduced functions of organs caused by inhibited blood circulation. More particularly, the present invention relates to an agent for improving the reduced functions of organs caused by inhibited blood circulation, which contains a particular organogermanium compound as an effective component.

2. Description of the Prior Art

In order for all organs of a living body to exhibit and maintain their functions, it is absolutely necessary that each of these organs be provided with a sufficient amount of blood. Accordingly, when the blood circulation to organs is inhibited for any reason, the organs as well as their functions inevitably have serious disorders.

A typical example of inhibited blood circulation to organs is a case in which a particular organ is separated from a living body for transplant.

That is, when organ separation and organ transplant are conducted at two different places which are geographically apart from each other, an organ separated from an organ donor is contained in a special vessel for storage, transferred and then transplanted. During the transfer, the separated organ is immersed in a special solution and kept at low temperatures but blood circulation to the organ is apparently inhibited. Accordingly, some reduction in functions of the organ during the transfer is anticipated.

Reduced functions of organs due to inhibited blood circulation are not restricted to separated organs. They are also seen in unseparated organs within a living body and, in the case of kidney, often appear as a disorder called "renal insufficiency".

Renal insufficiency can be largely classified into acute renal insufficiency and chronic renal insufficiency. Both insufficiencies refer to a state in which the kidney does not function normally. When renal insufficiency develops into a serious disorder, it takes a form of uremia. Uremia appears as hypouresis, hyperazotemia, hypertension, edema, various digestive system disorders (nausea, emesis, diarrhea, anorexia), anemia, bleeding, various neuraxial disorders (unrest, spasm, lethargy), etc. When uremia is left untreated, it leads to death in some cases.

Acute renal insufficiency is caused by shock (e.g. circulation insufficiency as mentioned above), drugs, etc. and chronic renal insufficiency is caused by glomerulonephritis or by chronic renal disorder derived from diabetes, drugs, etc. Therefore, in the treatment of acute renal insufficiency, the causes must be removed primarily. The only other treatment is to wait for the natural recovery of kidney function. In the treatment for chronic renal insufficiency, when the insufficiency is caused by disorder of the urinary organs, the causes must be removed primarily by operation.

As mentioned above, renal insufficiency, when left untreated, may develop into uremia which may lead to death. Therefore, it is necessary not only to remove the cause of the renal insufficiency but also to effect a wide range of treatments for renal insufficiency.

Currently, however, only hypertension, hyperphosphatemia, protein intake, etc. are being controlled for the treatment of chronic renal insufficiency. For the treatment of acute renal insufficiency, the administration of a diuretic, calcium antagonist, etc. is being tried, but the effect is questionable. It is said that there is yet no effective and universal method for internally treating either acute renal insufficiency or chronic renal insufficiency.

Thus, the reduced function of organs caused by inhibited blood circulation have heretofore been treated only by removing the cause and waiting for the natural restoration of the original functions. There exists no method for actively preventing the reduction in organ function or actively restoring the reduced functions.

SUMMARY OF THE INVENTION

In view of the foregoing prior art, the present invention has been made in order to provide a drug capable of effectively improving the reduced function of organs caused by inhibited blood circulation.

Another object of the present invention is to provide an agent for improving the reduced function of organs caused by inhibited blood circulation; the agent has no toxicity and no side effects.

The constitution adopted by the present invention in order to achieve the above objects lies in an agent for improving the reduced function of organs caused by inhibited blood circulation, characterized by containing, as an effective component, an organogermanium compound represented by the formula (I)

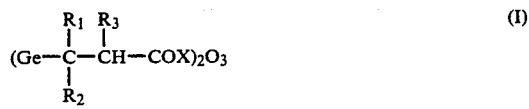

wherein $R_1$ to $R_3$ are each a hydrogen atom, a lower alkyl group such as methyl, ethyl or the like which may be the same or different, or a substituted or unsubstituted phenyl group, and X is a hydroxyl group, an O-lower alkyl group, an amino group or $O^-Y^+$. Y is a metal such as sodium, potassium or the like, or a basic group-containing compound such as lysozyme, basic amino acid or the like.

DETAILED DESCRIPTION OF THE PREFERRED EMBODIMENTS

Figure 1:
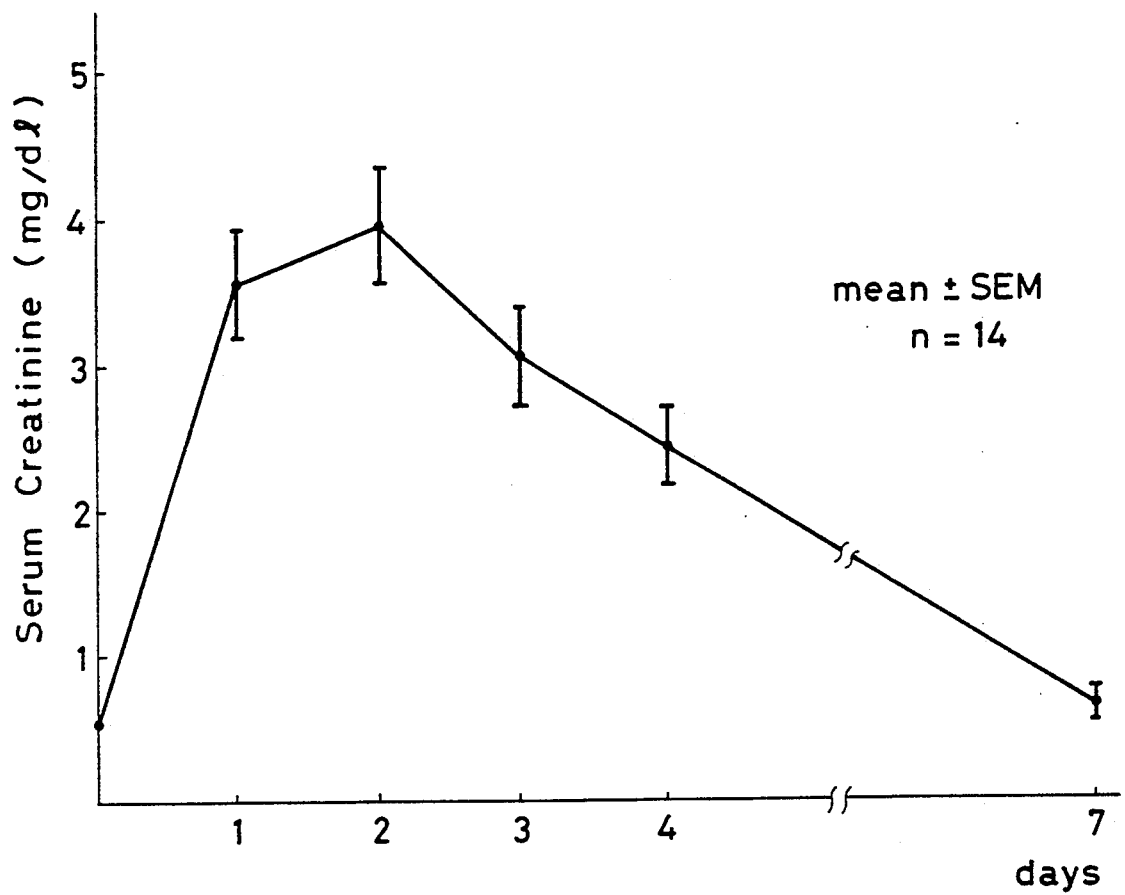
FIG. 1 is a graph showing that kidney functions are reduced by warm ischemia.

The agent for improving the reduced function of organs caused by inhibited blood circulation according to the present invention contains, as an effective component, a particular organogermanium compound represented by the formula (I). Hence, this compound is explained first. The compound has, as its basic skeleton, a germylpropionic acid formed by the bonding of a germanium atom and a propionic acid derivative having three substituents $R_1$ to $R_3$ and an oxygen functional group OX, in which the basic skeleton of the germanium atom and the oxygen atom is 2:3.

The substituents $R_1$ to $R_3$ are each a hydrogen atom, a lower alkyl group such as methyl, ethyl, propyl, butyl or the like, or a substituted or unsubstituted phenyl group; the substituent X is a hydroxyl group, an O-lower alkyl group, an amino group or a salt of carboxylic acid represented by $O^-Y^+$.

Y is a metal such as sodium, potassium or the like (the metal is not restricted to a monovalent metal), or a basic group containing a compound such as lysozyme, basic amino acid such as lysine or the like.

The substituents $R_1$ and $R_2$ bond to the a-position of the germanium atom and the substituent $R_3$ bonds to the b-position of the germanium atom. Accordingly, specific examples of the organogermanium compound used in the agent for improving the reduced functions of organs caused by inhibited blood circulation according to the present invention are as follows.

 (11)

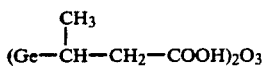 (12)

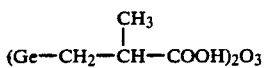 (13)

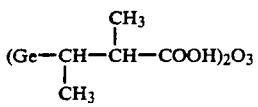 (14)

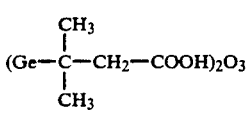 (15)

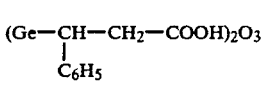 (16)

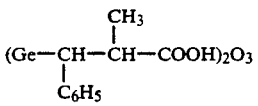 (17)

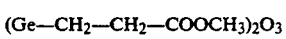 (18)

 (19)

 (20)

The organogermanium compounds having the above structures can be produced accordingly various methods.

Those compounds of the formula (I) wherein X=OH can be produced, for example, by hydrolyzing a trihalogermylpropionic acid already having three substituents $R_1$ to $R_3$, such as trichlorogermylpropionic acid (1), as shown in the following reaction formula.

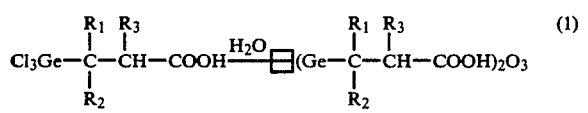 (1)

Those compounds of the formula (I) wherein is a lower alkyl group can be produced, for example, by reacting the above compound (I) with thionyl chloride or the like to convert the former to a corresponding acid halide, reacting the acid halide with an alcohol corresponding to the lower alkyl group, and then hydrolyzing the reaction product. Those compounds of the formula (I) wherein $X=NH_2$ can be produced, for example, by reacting the above acid halide with $NH_3$ and then hydrolyzing the reaction product. Those compounds of the formula (I) wherein $X=O^-Y^+$ and Y=a metal can be produced by reacting above compound (1) with a corresponding metal hydroxide. Those compounds of the formula (I) wherein $X=O^-Y^+$ and Y=a basic group-containing compound can be produced according to an ordinary acid-base reaction.

The analytical results obtained for the thus produced organogermanium compounds using instrumental analysis methods such as NMR spectrometry, infrared spectroscopy and the like well support that they are compounds represented by the general formula (I).

The agent for improving the reduced functions of organs caused by inhibited blood circulation of the present invention containing, as an effective component, a particular organogermanium compound obtained by the above synthesis can be administered orally or parenterally. That is, when administered orally, it can take a form of tablet, powder, granule or the like and, when administered parenterally, it can be in a form for injection.

The organogermanium compound which is an effective component in the present agent is characterized by having very low toxicity and substantially no side effects and accordingly can be administered in a wide range of doses, for example, 20–200 mg/Kg/day.

As described above, the present agent can rapidly and effectively improve the reduced function of organs (e.g. acute renal insufficiency) caused by inhibited blood circulation. Administration of the present agent to mice in which warm ischemic acute renal insufficiency had been forcibly allowed to take place showed the rapid restoration of reduced kidney function.

Administration of the present agent to the above mice at different times showed that the most effective administration time was before blood circulation was restarted. Accordingly, the present agent is said to have the advantage of reducing the burden or damage upon the organs when blood circulation is restarted during a transplant operation.

The present invention is illustrated below by way of Examples.

EXAMPLE 1

(1) Experimental method

Male SD rats each weighing 280–320 g were subjected to anesthesia by Nembutal(trade name) and then subjected to laparotomy in the middle. The artery of the left kidney of each rat was clamped for 45 minutes to stop blood circulation and thereby to cause reversible warm ischemic acute renal insufficiency. Simultaneously, the right kidney was enucleated.

A solution as the present agent, containing 30 mg of the compound of the formula (I-1) was administered intravenously right before clamping and right before declamping. To the control group, only a physiological saline solution (0.5 ml) was administered.

Then, each rat was placed in a metabolism cage from the 24th hour to the 48th hour from declamping and the 72nd hour to the 96th hour from declamping to collect the rat's urine for 24 hours.

Further, blood was collected in the 24th hour, the 48th hour and 72nd hour from declamping. Each rat was sacrificed in the 96th hour from declamping.

(2) Results

As shown in FIG. 1, warm ischemia of 45 minutes increases the serum creatinine value substantially, thus greatly reducing kidney function. The serum creatinine value reached a peak in 24–48 hours.

Kidney function returned to a value before warm ischemia in 7 days, indicating that the forcibly caused acute renal insufficiency was reversible.

Figure 2:
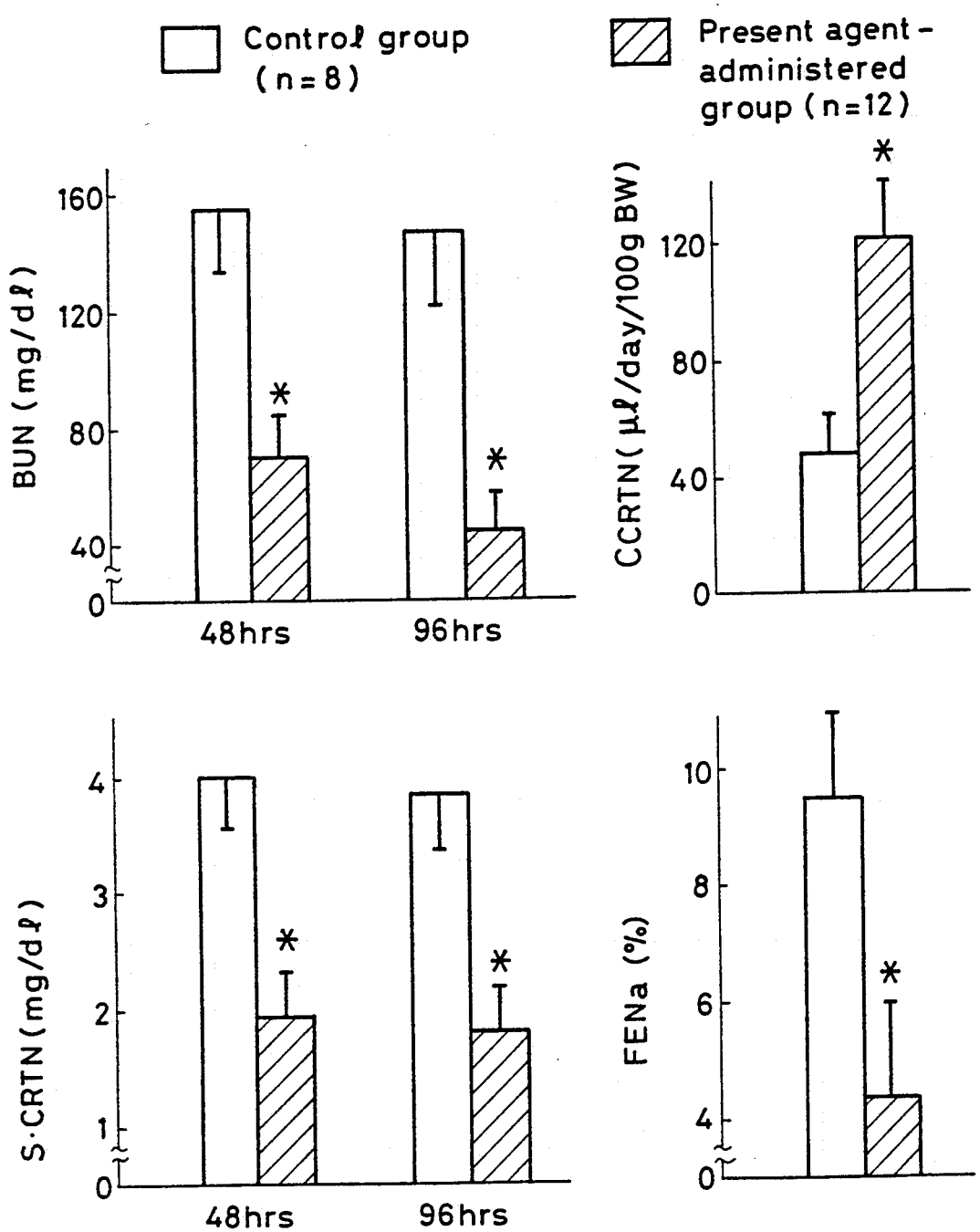
FIG. 2 are graphs showing that reduced kidney function are improved by the administration of the present agent.

As shown in FIG. 2, the BUN (blood-urea-nitrogen), S.CRTN (serum creatinine) and FENa (sodium reabsorption ratio) of the present agent-administered group were significantly lower than those of the control group. The C.CRTN (creatinine clearance) of the former group was significantly higher than that of the latter group. Thus the alleviation of the reduced kidney functions by the administration of the present agent was confirmed.

EXAMPLE 2

(1) Experimental method

The same method as in Example 1 was adopted with the following exception. That is, the present agent was administered only once right before the clamping or right before the declamping; in one group, the present agent was administered right before clamping and, in other group, the present agent was administered right before declamping.

(2) Results

Figure 3:
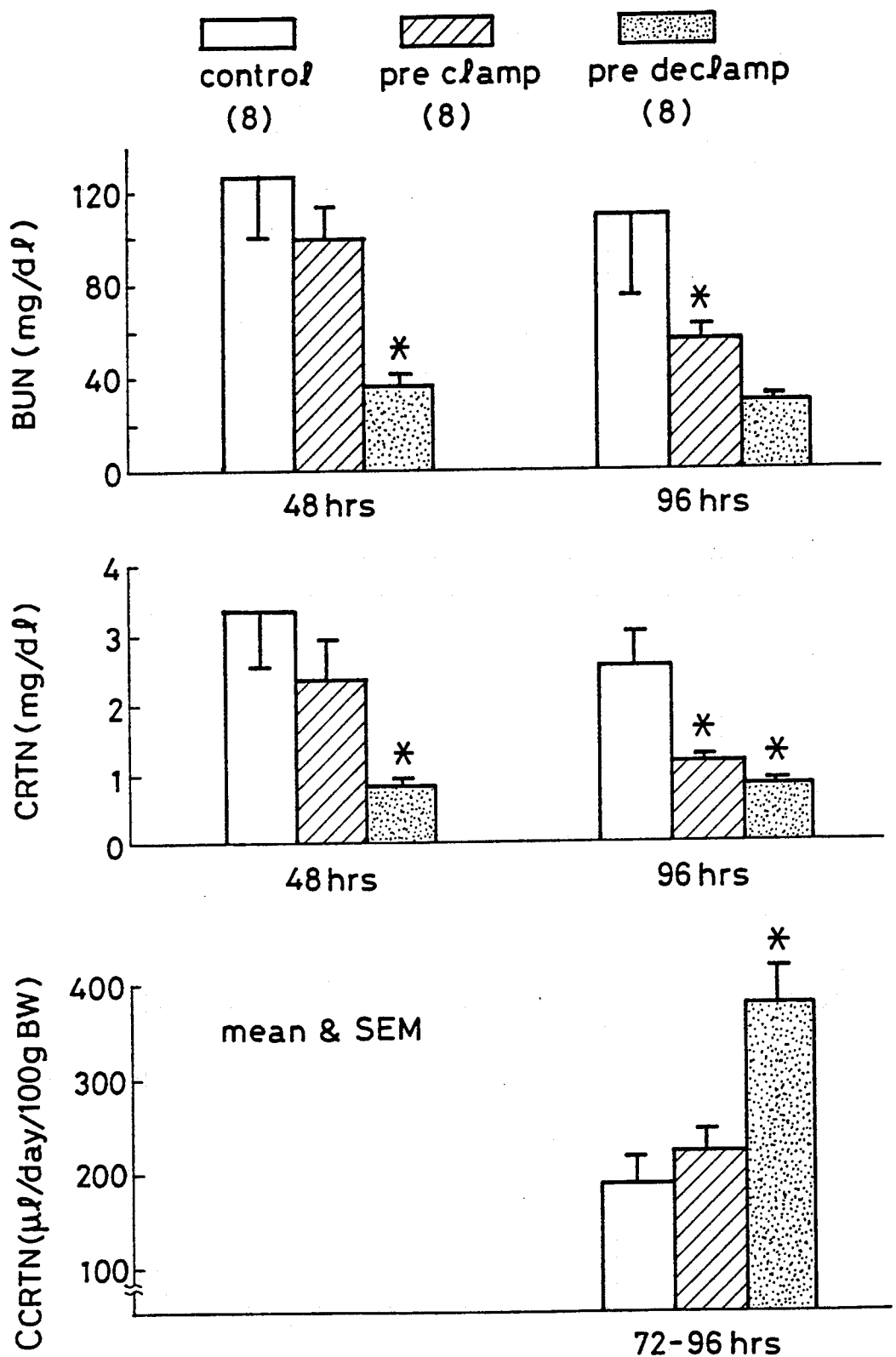
FIG. 3 are graphs showing the relationship between the time of administration and the effect of the agent of the present invention.

As shown in FIG. 3, in the group to which the present agent was administered right before clamping, the BUN and S.CRTN were reduced significantly in 96 hours as compared with the control group. In the group to which the present agent was administered right before declamping, the BUN and S.CRTN were reduced significantly in 48 hours as compared with the control group.

With regard to the increase in C.CRTN, the group to which the present agent was administered right before declamping showed a significant increase over the control group and the group to which the present agent was administered right before clamping.

Similar results were also obtained when other organogermanium compounds of the formula (I) were used.

As described above, the present agent is useful for the prevention of reduced function of organs caused by inhibited blood circulation.

What is claimed is:

1. A method for improving reversible ischemic renal insufficiency, said method comprising administering to a mammalian organism in need of such treatment, a therapeutically effective amount to improve reversible ischemic renal insufficiency of an organogermanium compound represented by the formula (I)

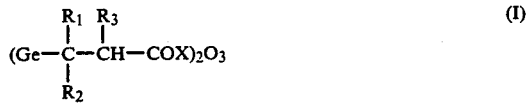

wherein $R_1$ to $R_3$ are each a hydrogen atom or a lower alkyl group which may be the same or different, or a phenyl group, and X is a hydroxyl group, a lower alkoxy group, a $-NH_2$ group or $O^-Y^+$ where Y is a metal or a basic group-containing compound or pharmaceutically acceptable salt thereof.

2. The method according to claim 1, wherein $R_1$, $R_2$, and $R_3$ are a hydrogen atom and X is a hydroxyl group.

3. The method according to claim 1, wherein the lower alkyl group for $R_1$ to $R_3$ is methyl, ethyl, propyl or butyl.

4. The method according to claim 1, wherein the metal is sodium or potassium.

5. The method according to claim 4, wherein the basic group-containing compound is lysozyme or a basic amino acid.

6. The method according to claim 5, wherein the basic amino acid is lysine.

* * * * *